United States Patent [19]

Dockner et al.

[11] 4,239,895

[45] Dec. 16, 1980

[54] PROCESS FOR PRODUCING 1-HYDROXYMETHYLIMIDAZOLES

[75] Inventors: Toni Dockner, Meckenheim; Anton Frank, Ludwigshafen; Uwe Kempe, Heidelberg; Matthias Wetzler; Helmut Karn, both of Ludwigshafen, all of Fed. Rep. of Germany

[73] Assignee: BASF Aktiengesellschaft, Fed. Rep. of Germany

[21] Appl. No.: 64,860

[22] Filed: Aug. 8, 1979

Related U.S. Application Data

[62] Division of Ser. No. 3,966, Jan. 16, 1979, abandoned.

[30] Foreign Application Priority Data

Jun. 10, 1978 [DE] Fed. Rep. of Germany ....... 2825547

[51] Int. Cl.$^3$ ............................................ C07D 233/60
[52] U.S. Cl. ..................................... 548/341; 548/342
[58] Field of Search ................................. 548/341, 342

[56] References Cited

U.S. PATENT DOCUMENTS 4,063,023  12/1977  Anderson et al. ................... 548/342

OTHER PUBLICATIONS

Ewins, Journal of the Chemical Society, vol. 99, pp. 2052–2059 (1911).
Durant et al., Journal of Medicinal Chemistry, vol. 19, pp. 923–928 (1976).

*Primary Examiner*—Alan L. Rotman
*Attorney, Agent, or Firm*—Keil & Witherspoon

[57] ABSTRACT

1-Hydroxymethylimidazoles which are unsubstituted or alkyl-substituted in the 2-position, their manufacture and their use as chemical intermediates, e.g. for other imidazole derivatives or for the drug cimetidine.

6 Claims, No Drawings

PROCESS FOR PRODUCING 1-HYDROXYMETHYLIMIDAZOLES

This is a division of application Ser. No. 3,966 filed Jan. 16, 1979, which application has now been abandoned.

The present invention relates to 1-hydroxymethylimidazoles which may be alkyl-substituted in the 2-position, their preparation and their use as chemical intermediates.

We have found that 1-hydroxymethylimidazoles of the formula 1

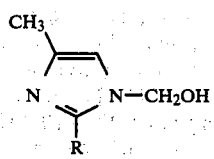

where R is hydrogen or alkyl of 1 to 18 carbon atoms, are chemical intermediates having valuable properties.

Compounds to be singled out particularly from amongst those of the formula 1 are those where R is alkyl of 1 to 4 carbon atoms, whilst the particularly preferred compound is that where R is hydrogen.

To prepare a compound of the formula 1, an imidazole of the formula 2

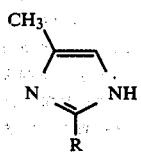

where R has the above meanings, is reacted with paraformaldehyde or trioxane at from 40° to 150° C., directly or in the presence of an aromatic hydrocarbon as the solvent.

The starting compounds are advantageously used in a molar ratio of 0.8–1:1–0.8, paraformaldehyde or trioxane being calculated as monomeric formaldehyde; the particularly preferred molar ratio is about 1:1.

The preferred reaction temperatures are from 50° to 70° C. The direct reaction is carried out in the melt of the starting materials. For carrying out the reaction in the presence of a solvent, suitable solvents include alkylbenzenes, eg. toluene or xylene, chlorobenzene and nitrobenzene. As a rule, the reaction is complete after 10–20 hours if a solvent is used, whilst the direct reaction in the melt is complete after 1–2 hours.

The process of preparation by direct hydroxymethylation at the nitrogen atom 1 gives a high yield and is free from interfering side-reactions. This result is surprising and was not foreseeable. Rather, it would have been expected that in addition to the 5-hydroxymethyl compound, substantial amounts of dihydrazopyrazine derivatives would be formed, in accordance with the equation given in Chemical and Pharmaceutical Bulletin, 22 (1975), 2359-64

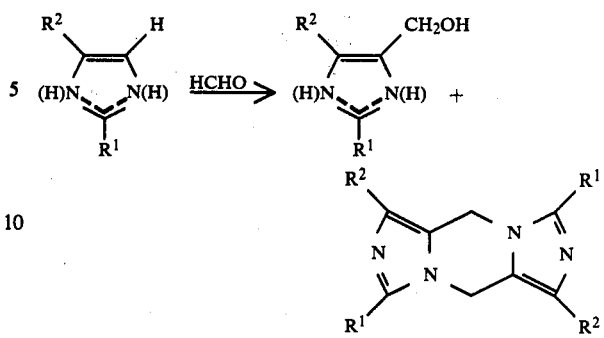

The compounds according to the invention are valuable chemicals which may be used, for example, as curing agents for epoxy resins, as emulsifiers for the preparation of water-in-oil emulsions, as lubricant additives or as intermediates for drugs for human or veterinary medicine.

4-Methyl-1-hydroxymethylimidazole is a new starting compound for the preparation of 4-methyl-5-[(2-aminoethyl)-thiomethyl]-imidazole, which in turn is an important intermediate for the preparation of the drug cimetidine (N-cyano-N'-methyl-N''-[2-((4-methyl-5-imidazolyl)-methylmercapto)ethyl]-guanidine), as described, for example, in German Laid-Open Applications DOS 2,344,779 and DOS 2,649,059.

To prepare the last-mentioned compound, 4-methyl-1-hydroxymethylimidazole is reacted with cysteamine in concentrated hydrochloric acid by boiling a solution of the said reactants in a 2-fold to 5-fold molar amount of concentrated hydrochloric acid for from 10 to 20 hours, distilling off the excess hydrochloric acid under reduced pressure and purifying the resulting crude 4-methyl-5-[(2-aminoethyl)thiomethyl]-imidazole dihydrochloride by recrystallization from alcohol.

The 1-hydroxymethylimidazoles of the formula 1 can also be rearranged to the corresponding 5-hydroxymethylimidazoles by heating in aqueous hydrochloric acid containing from 10 to 37, preferably from 13 to 25, % by weight of hydrogen chloride; a high yield is obtained. Using aqueous hydrochloric acid of the preferred concentration range, virtually no chloromethylation side reaction occurs.

The above rearrangement reaction takes place at atmospheric pressure by heating, advantageously at from 80° C. to the boiling point of the solution, and is as a rule complete after from 10 to 120 hours. It may be advantageous to carry out the reaction in a closed vessel under a pressure slightly above atmospheric, of up to 2 bar, and at up to 125° C. This rearrangement reaction can, if desired, also be carried out in an aqueous-alcoholic solution of hydrogen chloride, in which case up to 50% by volume of ethyl alcohol may advantageously be present.

This surprisingly smooth rearrangement constitutes a process for the preparation of 5-hydroxymethylimidazoles of the formula 3

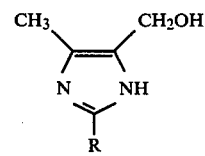

where R has the above meanings.

It is known that certain 5-hydroxymethylimidazoles can only be prepared with difficulty. For example, 4-methyl-5-hydroxymethylimidazole is prepared from 4-methylimidazole-5-carboxylic acid esters by a rather involved method, entailing reduction with lithium aluminum hydride [J. Med. Chem. 19 (1976) 923–928] or with alkali metals or calcium in liquid ammonia (German Laid-Open Application DOS 2,637,670).

4-Methyl-5-hydroxymethylimidazole, obtained by rearrangement of the 1-hydroxymethyl compound, can be reacted in the conventional manner with cysteamine in boiling concentrated aqueous hydrochloric acid to give 4-methyl-5-[(2-aminoethyl)-thiomethyl]-imidazole, the well-known intermediate for cimetidine. In a particularly advantageous and economical embodiment, the reaction is carried out with 2,2-dimethylthiazolidine instead of with cysteamine.

EXAMPLE 1

1-Hydroxymethyl-4-methylimidazole 410 g (=5 moles) of 4-methylimidazole in 2 liters of toluene are heated to 50° C. 150 g of paraformaldehyde are introduced into the solution and dissolved, giving a weakly exothermic reaction, with the temperature rising from 50° to 55° C.). The mixture is then stirred for 17 hours at 50°–55° C. and cooled to 0°–5° C. in an icebath, and the crystals are filtered off and dried under reduced pressure.

The yield of 532 g corresponds to 95.0% of theory, melting point 65°–67° C.

| Elementary analysis: | | | | |
| --- | --- | --- | --- | --- |
|  | C | H | N | O |
| calculated: | 53.55% | 7.18% | 24.98% | 14.27% |
| found: | 53.3% | 7.3% | 24.8% | 15.1% |

EXAMPLE 2

30 g of paraformaldehyde are added in portions to 82 g of 4-methylimidazole at 60°–65° C. and the mixture is left at this temperature for 1 hour, during which the paraformaldehyde dissolves completely. When the reaction mixture has cooled, it is pulverized. 112 g of 1-hydroxymethyl-4-methylimidazole (corresponding to the theoretical yield) of melting point 59°–60° C. are obtained.

EXAMPLE 3

110 g of 2-ethyl-4-methylimidazole are dissolved in 400 ml of toluene at 50° C. 30 g of paraformaldehyde are introduced into this solution, whilst stirring. The mixture is then stirred for 16 hours at 50°–55° C. and is cooled in an icebath, and the crystal slurry is filtered off. The resulting crude product is recrystallized from 300 ml of acetone. 130 g of 1-hydroxymethyl-2-ethyl-4-methylimidazole (corresponding to a yield of 92.9% of theory), of melting point 83.1°–86.3° C., are obtained.

EXAMPLE 4

192.0 g of 2,4-dimethylimidazole are dissolved in 1.5 liters of toluene and 60.0 g of paraformaldehyde are added at 50° C. The paraformaldehyde dissolves and after about 15 minutes a thick white precipitate separates out. The mixture is stirred for a further 30 minutes at 50°–60° C. and is cooled in an icebath, and the crystals are filtered off.

After drying under reduced pressure, 250 g of 1-hydroxymethyl-2,4-dimethylimidazole (corresponding to a yield of 99.2% of theory), of melting point 110.5°–111° C., are obtained.

EXAMPLE 5

4-Methyl-5-hydroxymethylimidazole hydrochloride 560 g (=5 moles) of 1-hydroxymethyl-4-methylimidazole are introduced into 2,250 g of concentrated hydrochloric acid at 25° C., with cooling, and the mixture is then refluxed for 17 hours. The hydrochloric acid is distilled off, as completely as possible, under reduced pressure and the residue is recrystallized from 2.5 liters of alcohol. 340 g of crystals of melting point 207°–214° C. are obtained. The filtrate is concentrated and cooled in an icebath, and gives a further 192 g of crystals of melting point 202°–211° C. Yet a further 48 g of crystals, of melting point 202°–209° C., are obtained by concentrating the residual filtrate and then cooling it.

The total yield of 580 g of 4-methyl-5-hydroxymethylimidazole hydrochloride, containing 5–10% of the chloromethyl compound, corresponds to a yield of about 71% of theory.

EXAMPLE 6

2-Ethyl-4-methyl-5-hydroxymethylimidazole 45 g of 1-hydroxymethyl-2-ethyl-4-methylimidazole are introduced into a mixture of 100 g of 36% strength hydrochloric acid and 100 g of water and the reaction solution is refluxed for 17 hours. It is then evaporated under reduced pressure and the residue is recrystallized from ethanol. 39 g of 2-ethyl-4-methyl-5-hydroxymethylimidazole hydrochloride (corresponding to a yield of 68.8% of theory), of melting point 124.3°–125.5° C., are obtained.

EXAMPLE 7

126 g of 1-hydroxymethyl-2,4-dimethylimidazole are introduced into a mixture of 300 g of concentrated hydrochloric acid and 300 g of water and the batch is refluxed for 17 hours. The hydrochloric acid is then distilled off under reduced pressure and the residue is recrystallized from ethanol. 130 g of 2,4-dimethyl-5-hydroxymethylimidazole hydrochloride (corresponding to a yield of 80.0% of theory), of melting point 237°–238° C., are obtained.

EXAMPLE 8

4-Methyl-5-[(2-aminoethyl)-thiomethyl]-imidazole dihydrochloride 30 g of 4-methyl-5-hydroxymethylimidazole hydrochloride and 23 g of cysteamine in 450 ml of concentrated hydrochloric acid are refluxed for 17 hours. The solution is evaporated to dryness under reduced pressure. The residue (61 g) is recrystallized from 500 ml of alcohol. 41 g of 4-methyl-5-[(2-aminoethyl)-thiomethyl]imidazole dihydrochloride (corresponding to a yield of 84.0% of theory), of melting point 184°–191° C., are obtained.

EXAMPLE 9

112 parts of 1-hydroxymethyl-4-methylimidazole and 1,080 parts of 15% strength aqueous hydrochloric acid are heated for 48 hours at 125° C. under 2 bar pressure. The reaction mixture is evaporated under reduced pressure, the residue (157 parts) is dissolved in 500 parts of water, and the solution is brought to pH 8.6 with about 50 ml of 50% strength sodium hydroxide solution. The resulting solution is filtered and evaporated under reduced pressure, and the residue (173 parts) is boiled up with 250 parts of methanol and filtered off after cooling. The solid is washed with 50 parts of methanol and the filtrate is evaporated under reduced pressure. 120 parts of evaporation residue are obtained; this material is dissolved in 240 parts of hot 2-propanol, and the solution is filtered. The filtrate is cooled overnight at 0°–5° C. and the crystals are filtered off and dried. 68 parts of 4-methyl-5-hydroxymethylimidazole of melting point 122°–130° C. are obtained. The mother liquor is concentrated to half its volume under reduced pressure and the residue is cooled overnight at 0°–5° C. This causes a further 18 parts of 4-methyl-5-hydroxymethylimidazole to separate out. The total yield is 86 parts, corresponding to 76.8% of theory. The product can be further purified by recrystallization from 2-propanol. The pure compound melts at 137°–138° C. and gives a spot at $R_F=0.54$ in a thin layer chromatogram.

Thin layer chromatography: Plate: Merck Kieselgel 60 F 254 Solvent: 70 parts of chloroform + 50 parts of methanol Development: iodine chamber.

EXAMPLE 10

4-Methyl-5-[(2-aminoethyl)-thiomethyl]-imidazole dihydrochloride 108 g of 4-methyl-5-hydroxymethylimidazole hydrochloride (=20 mole % excess) and 72 g of 2,2-dimethylthiazolidine are introduced into 1,350 ml of concentrated hydrochloric acid, whilst cooling to 20°–30° C. The mixture is refluxed for 17 hours and then evaporated to dryness under reduced pressure. The residue obtained (235 g) is recrystallized from 400 ml of alcohol.

144 g of 4-methyl-5-[(2-aminoethyl)-thiomethyl]-imidazole dihydrochloride (corresponding to a yield of 98.1% of theory), of melting point 185°–192.5° C., are obtained.

EXAMPLE 11 (COMPARATIVE EXAMPLE)

41 g of 4-methylimidazole, 38.5 g of cysteamine and 15 g of paraformaldehyde in 240 ml of concentrated hydrochloric acid are refluxed for 17 hours. The hydrochloric acid is distilled off under reduced pressure and the residue is recrystallized from alcohol. The yield is 47 g of thiazolidine hydrochloride of melting point 135°–155° C.; according to elementary analysis and NMR spectroscopy the product contains about 10% of 4-methyl-5-[(2-aminoethyl)thiomethyl]-imidazole dihydrochloride.

The Comparative Example shows that in this reaction only a small proportion of the desired compound is formed.

EXAMPLE 12

30 g of paraformaldehyde are added in portions to 82 g of 4-methylimidazole at 50° C., whilst stirring. After 1 hour, all the paraformaldehyde has dissolved. The melt is added dropwise to a solution of 113 g of cysteamine hydrochloride in 450 g of concentrated hydrochloric acid and the mixture is refluxed for 17 hours. It is then evaporated under reduced pressure and the residue obtained is recrystallized twice from ethanol.

160 g of 4-methyl-5-[(2-aminoethyl)-thiomethyl]-imidazole dihydrochloride (corresponding to a yield of 65.5% of theory), of melting point 185°–192° C., are obtained.

EXAMPLE 13

90 g of 4-methyl-5-hydroxymethylimidazole hydrochloride (0.6 mole) and 70 g of 2,2-dimethylthiazolidine (technical grade, 78.8% pure, 0.47 mole) are introduced into 1,350 ml of concentrated aqueous hydrochloric acid, whilst cooling to 20° C. The mixture is refluxed for 17 hours and then evaporated to dryness under reduced pressure, and the residue is recrystallized from ethyl alcohol.

106 g of 4-methyl-5-[(2-aminoethyl)-thiomethyl]-imidazole dihydrochloride (corresponding to a yield of 92.4% of theory based on 2,2-dimethyl-thiazolidine), of melting point 182.2°–191.2° C., are obtained. The IR spectrum is identical with that of the compound of Example 9.

We claim:

1. A process for the preparation of a compound of the formula 1

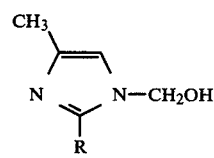

where R is hydrogen or alkyl of 1 to 18 carbon atoms, which comprises: reacting an imidazole of the formula 2

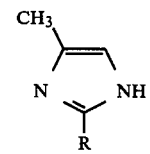

where R has the meanings given above, with paraformaldehyde or trioxane, at from 40° to 150° C.

2. The process of claim 1 wherein the reaction is carried out in the presence of an aromatic hydrocarbon as a solvent.

3. The process of claim 2 wherein the molar ratio of compound 2 to paraformaldehyde or trioxane calculated as monomeric formaldehyde is from 0.8-1:1-0.8.

4. The process of claim 3 wherein the reaction is carried out at a temperature of from 50° to 70° C.

5. The process of claim 1 wherein the process is carried out in the absence of a solvent, and wherein the molar ratio of compound 2 to paraformaldehyde or trioxane calculated as monomeric formaldehyde is from 0.8-1:1-0.8.

6. A process for the preparation of 5-hydroxymethylimidazole in which a compound I prepared by the process of claim 1 is rearranged to 5-hydroxymethylimidazole by heating said compound I in aqueous hydrochloric acid.

* * * * *